(12) United States Patent
Nyarady

(10) Patent No.: US 8,696,586 B2
(45) Date of Patent: Apr. 15, 2014

(54) METHOD AND DEVICE FOR MEASURING BLOOD FLOW IN THE BONE AFTER A FRACTURE

(76) Inventor: Jozsef Nyarady, Pecs (HU)

( * ) Notice: Subject to any disclaimer, the term of this patent is extended or adjusted under 35 U.S.C. 154(b) by 1300 days.

(21) Appl. No.: 12/114,859

(22) Filed: May 5, 2008

(65) Prior Publication Data

US 2008/0312545 A1 Dec. 18, 2008

Related U.S. Application Data

(60) Provisional application No. 60/915,885, filed on May 3, 2007.

(51) Int. Cl.
*A61B 1/317* (2006.01)
*A61B 5/026* (2006.01)

(52) U.S. Cl.
USPC ............. 600/504; 623/23.11; 623/23.12; 623/23.15; 606/65; 606/89

(58) Field of Classification Search
None
See application file for complete search history.

(56) References Cited

U.S. PATENT DOCUMENTS

| | | | | |
|---|---|---|---|---|
| 5,513,662 A | * | 5/1996 | Morse et al. | 128/898 |
| 6,086,542 A | * | 7/2000 | Glowa et al. | 600/561 |
| 2003/0055316 A1 | * | 3/2003 | Brannon | 600/114 |

OTHER PUBLICATIONS

Köster et al. (Archives of Orthopedic and Trauma Surgery. 1999; 119: 245-252).*

* cited by examiner

*Primary Examiner* — Shanon A Foley
(74) *Attorney, Agent, or Firm* — Young & Thompson

(57) ABSTRACT

A method and device for measuring blood flow in the bone after a fracture, wherein a hole is drilled into the bone. The method includes the steps of inserting the metal sleeve of an osteoscope into the hole; inserting the optics of an osteoscope into the metal sleeve and focused on the cavity created by the drill; filling the device and the cavity with a physiological solution such that the pressure of the solution is above the systolic blood pressure; decreasing the pressure of the solution while observing the cavity through the osteoscope, and recording the pressure in the system at the commencement of bleeding.

17 Claims, 6 Drawing Sheets a) from ventral    b) from dorsal a)

b)

Fig. 5a-5m cont'd
h)
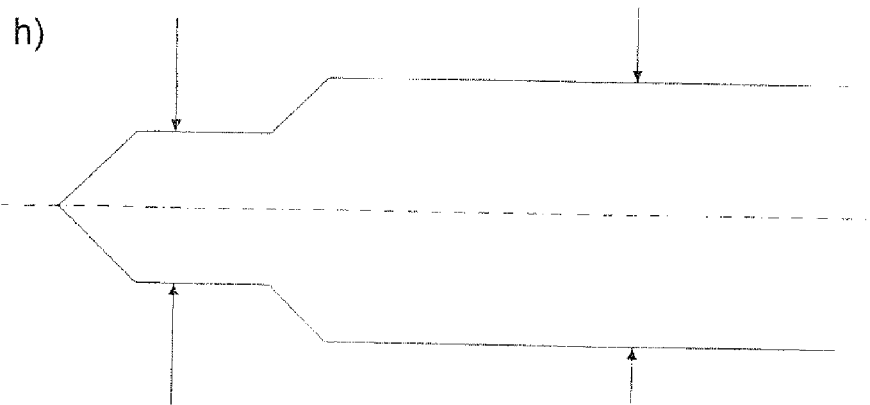
i)
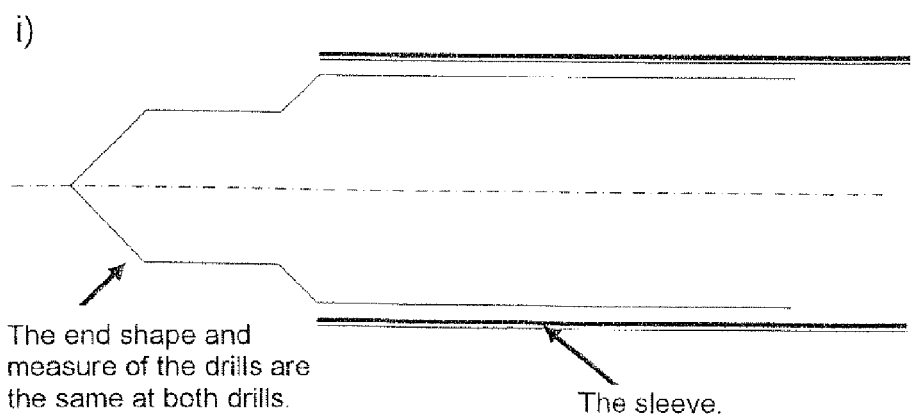
The end shape and measure of the drills are the same at both drills.
The sleeve.
j)
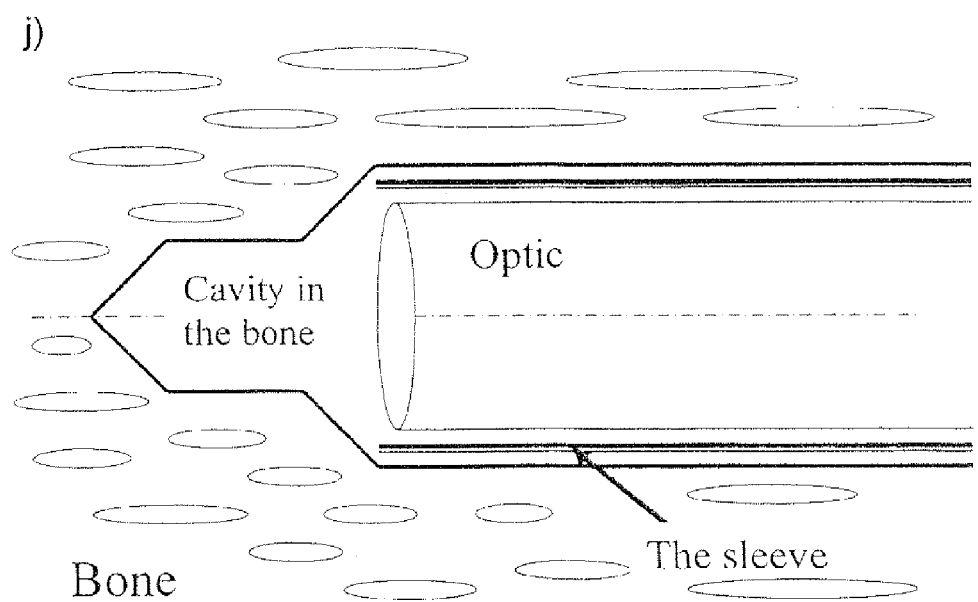

METHOD AND DEVICE FOR MEASURING BLOOD FLOW IN THE BONE AFTER A FRACTURE

BACKGROUND OF THE INVENTION

1. Field of the Invention

The present invention relates to a method for measuring blood flow in the bone after a fracture, typically a femoral neck fracture, wherein a hole is drilled into the bone, preferably through the neck of the femur into the head of the femur. The invention also relates to a device for measuring blood flow in the bone after a fracture, typically a femoral neck fracture.

2. Description of the Related Art

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Often the circulation of the bone, mainly the femoral head is destroyed at a dislocated bone fracture, typically at a femoral neck fracture. If there is inadequate circulation, a necrosis of the femoral head will develop and prosthesis implantation is the most likely course of treatment. Inadequate blood flow in the neck of the femur may lead to inadequate healing of the femoral head after a fracture, as well as cause osteonecrosis, a disease that results from loss of blood supply to the bone where the bone tissue dies and may eventually collapse. If a bone involved in osteonecrosis is near a joint, such as in the case of the femoral head, it often leads to the collapse of the joint surface. Conversely, if there is adequate circulation of the femoral head, the femoral head remains alive and in this way the fracture is capable of healing. In this instance, the most likely surgical solution is to perform osteosynthesis. Thus, the determination of whether there is adequate circulation is an important step in the overall treatment regimen.

Presently, the two most widely used methods for evaluating circulation are angiographic and isotopic methods. However, neither method is effective as the isotope or contrast material flows out of the head of the femur and into the fracture gap. Because the material covers the site to be examined, the examination can only be performed two weeks after the neck fracture. Abnormal blood flow patterns in the bone within a few weeks of a fracture may provide early warning of delayed union or nonunion of the fracture (Ashroft, et al.; "Measurement of Blood Flow in Tibial Fracture Patients Using Positron Emission Tomography," J Bone Joint Surg [Br] 1992; 74-8: 673-677).

A method for measuring blood flow in the bone before surgery will impact treatment selection, which will likely result in improvement of clinical outcome, minimization of cost and prevention of long term disability (Research Study, "Fracture healing—measuring blood in bone using MRI." Department of Orthopaedics, MEMO, Department of Clinical Radiology at Bristol Infirmary, and Department of Cardiovascular Medicine, John Radcliffe, Oxford). Furthermore, accurate measurement of blood flow is important for orthopaedic research due to close correlation of the flow with bone formation and mineral deposition. Accurate measurements may also allow secondary predictions of bone activity in other bone disoeders.

Bone imaging techniques, including scintigraphy and magnetic resonance imaging, have also been employed by some investigators to determine the blood supply available to the femoral head prior to surgery, these techniques have not been successful.

Watanabe Y, Terashima Y, Takenaka N, Kobayashi M and Matsushita T suggested to measure the intramedullary oxygen tension of the proximal femur after a femoral neck fracture and to evaluate the usefulness of that monitoring for prediction of subsequent avascular necrosis (J Orthop Trauma. 2007 August; 21 (7); 456-61).

Cho M R, Lee S W, Shin D K, Kim S K, Kim S Y, Ko S B, Kwun K W used 7.0 mm cannulated screws for fracture fixation to monitor bleeding (J Orthop Trauma. 2007 March; 21(3):158-64).

A 2.0-millimeter drill was used to assess the presence and character of bleeding from the femoral head at open reduction and internal fixation of a femoral neck fracture, according to Gill T J, Sledge J B, Ekkernkamp A, Ganz R (Orthop Trauma. 1998 September-October; 12(7):474-8).

These techniques, however, often do not provide as detailed and accurate information as the intraoperative techniques, which albeit invasive have been preferred and employed recently. A major limitation of the intraoperative invasive techniques, however, is that assessment of vascularity in the femoral head is often not sufficiently quantitative for routine clinical use.

Thus, there is presently a great need for a method and instrument that can give an accurate and more immediate determination of circulation flow.

SUMMARY OF THE INVENTION

In accordance with this invention, a method is suggested for measuring blood flow in the bone after a femoral neck fracture, wherein a hole is drilled through the neck of the femur into the head of the femur, a metal sleeve is inserted into to the hole; the optics of an osteoscope is inserted into the metal sleeve and focused on the cavity created by the drill; the device and the cavity is filled with a physiological solution such that the pressure of the solution is above the systolic blood pressure; the pressure of the solution is decreased while observing the cavity through the osteoscope, and at the commencement of bleeding, the pressure in the system is recorded. Preferably the hole is flushed out before filled with physiological solution.

The metal sleeve is preferably inserted into the hole to leave free the wall of a small part of the cavity, wherein the diameter of the small part of the cavity is drilled to be smaller, than the internal diameter of the sleeve and the surface of the small part of the cavity is at least 30 mm$^2$, preferably at least 35 mm$^2$, most preferably at least 40 mm$^2$.

According to an aspect of the invention, the optics is arranged in the sleeve to be about 2 mm shorter, than the sleeve.

Preferably, a second drill is used through the hole of the sleeve thereby removing fragments of the bone.

According to the invention, acceptable circulation is recorded when the difference between the systolic pressure and the measured pressure is less than 60 mm Hg, and unacceptable circulation is recorded when the difference in the pressure is more than 60 mm Hg.

Another object of the invention is a device to measure blood flow in the bone after a femoral neck fracture, which includes a metal sleeve to be inserted into a bore drilled in the fractured bone; the optics of an osteoscope to be inserted into said metal sleeve and connected to a visual display; a reservoir with physiological solution connected to the metal sleeve; means for controlling the pressure of the solution; a manometer for monitoring the pressure of the solution; and a manometer for measuring the blood pressure of the patient. The metal sleeve has preferably a flow in connection and a flow out connection to the reservoir with physiological solution and the device is provided with a flushing fluid pump and a flushing fluid collection container as well.

According to a preferred embodiment, a first drill is provided with an external diameter approximately the same size as the external diameter of the sleeve and a second drill is provided with an external diameter approximately the same size as the internal diameter of the sleeve, wherein the drills are provided with end sections having smaller diameter, than the internal diameter of the sleeve. The end section is at least 1 mm long.

The osteoscope applied in the device according to the invention is preferably an osteoscope with 0° optics and is at least 150 mm long, preferably 450 mm long and most preferably 550 mm long.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

As disclosed herein, the invention relates to a device and method for the measurement of blood flow in the bone.

All references cited herein are incorporated by reference in their entirety as though fully set forth. Unless defined otherwise, technical and scientific terms is used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

Figures 1A, 1B:
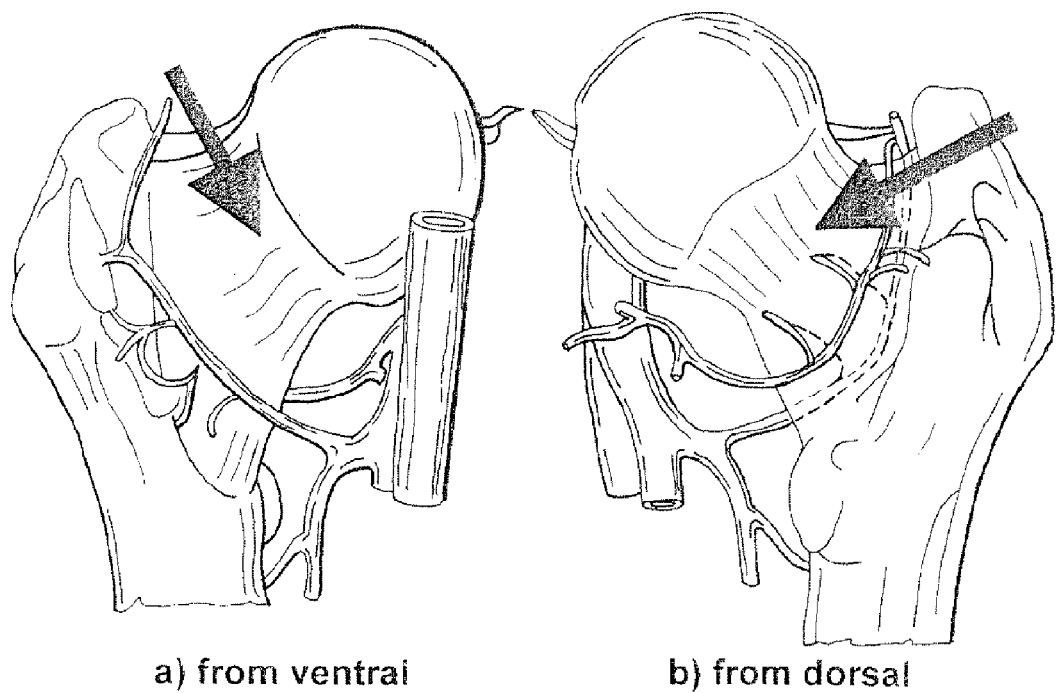
FIG. 1 (prior art) depicts the blood supply of the femoral head. The arteries and veins are running on the surface of the femoral neck, as depicted by the arrows.
Figure 2:
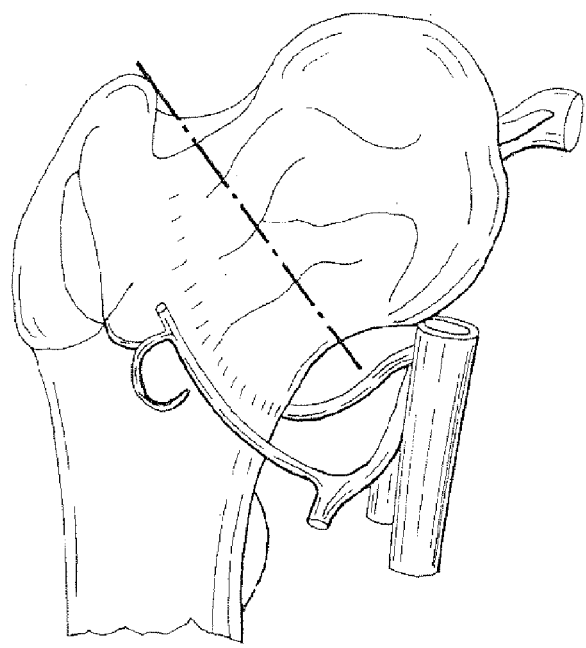
FIG. 2 (prior art) depicts the femoral neck. In cases of dislocated femoral neck fracture the vessels are destroyed. The line depicts the line of a fracture.
Figures 3A, 3B, 3C, 3D, 3E:
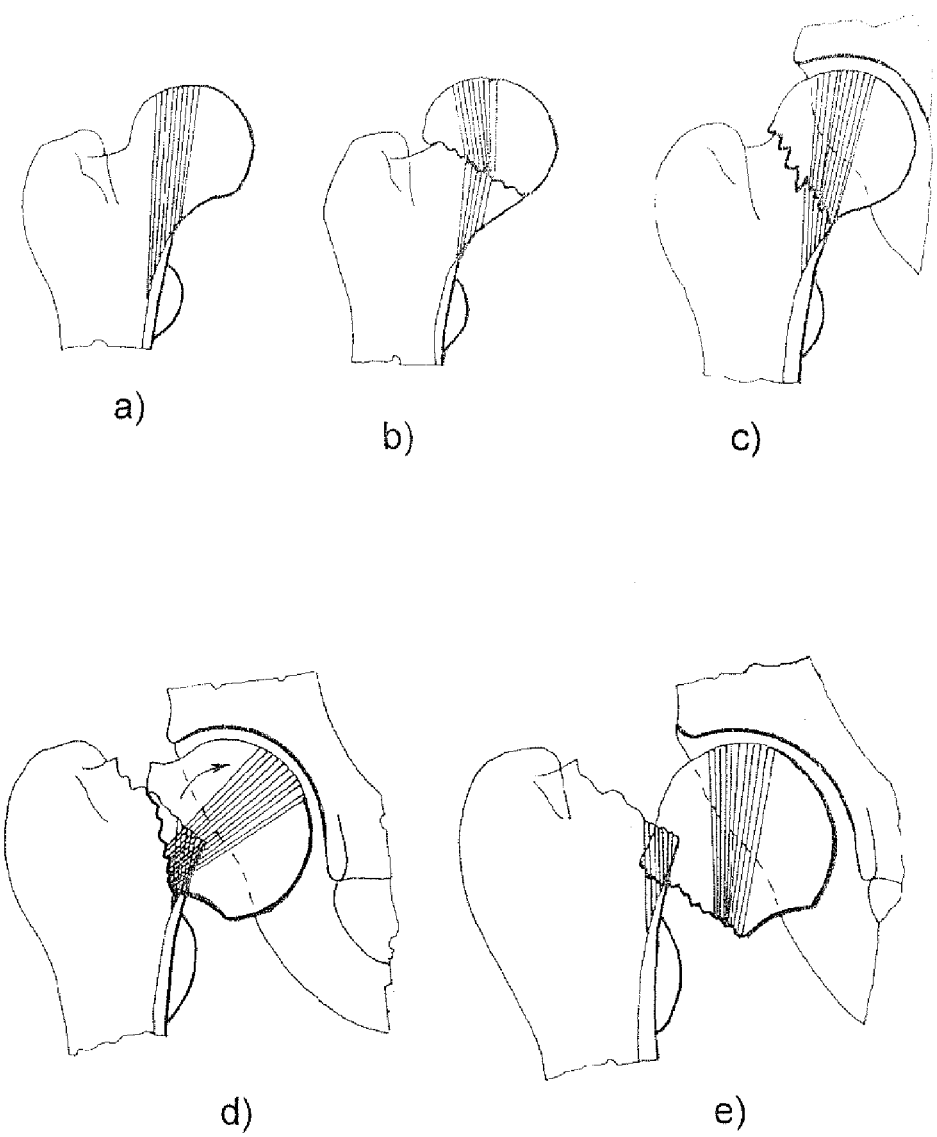
FIG. 3 (prior art) depicts the femoral neck fracture as classified by the Garden classification as used in clinical practice. In the cases of Garden I and II (as depicted by "1" and "2", respectively), there is no dislocation and the circulation is intact. In the cases of Garden III and IV (as depicted by "3" and "4", respectively), there is dislocation and the circulation may or may not be destroyed.
Figure 4A:
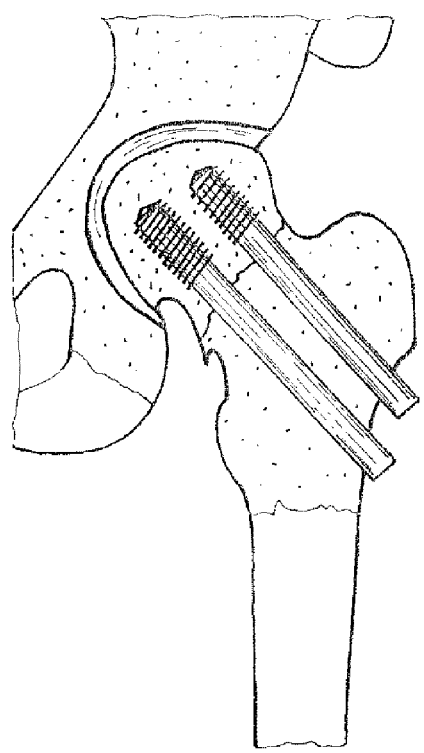
FIG. 4 (prior art) depicts X-ray pictures of the femur head under two different treatment scenarios. As depicted in (a), if the circulation of the head is intact after the neck fracture, the surgical method used is the preservation of the head (osteosynthesis). As depicted in (b), if the circulation of the head is destroyed after the neck fracture, the surgical method used is head replacement (prosthesis implantation).
Figure 4B:
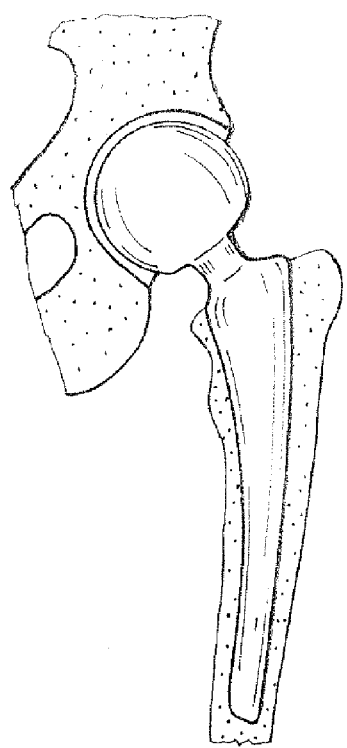
Figures 5A, 5B, 5C, 5D, 5E, 5F, 5G, 5H, 5I, 5J, 5K, 5L, 5M:
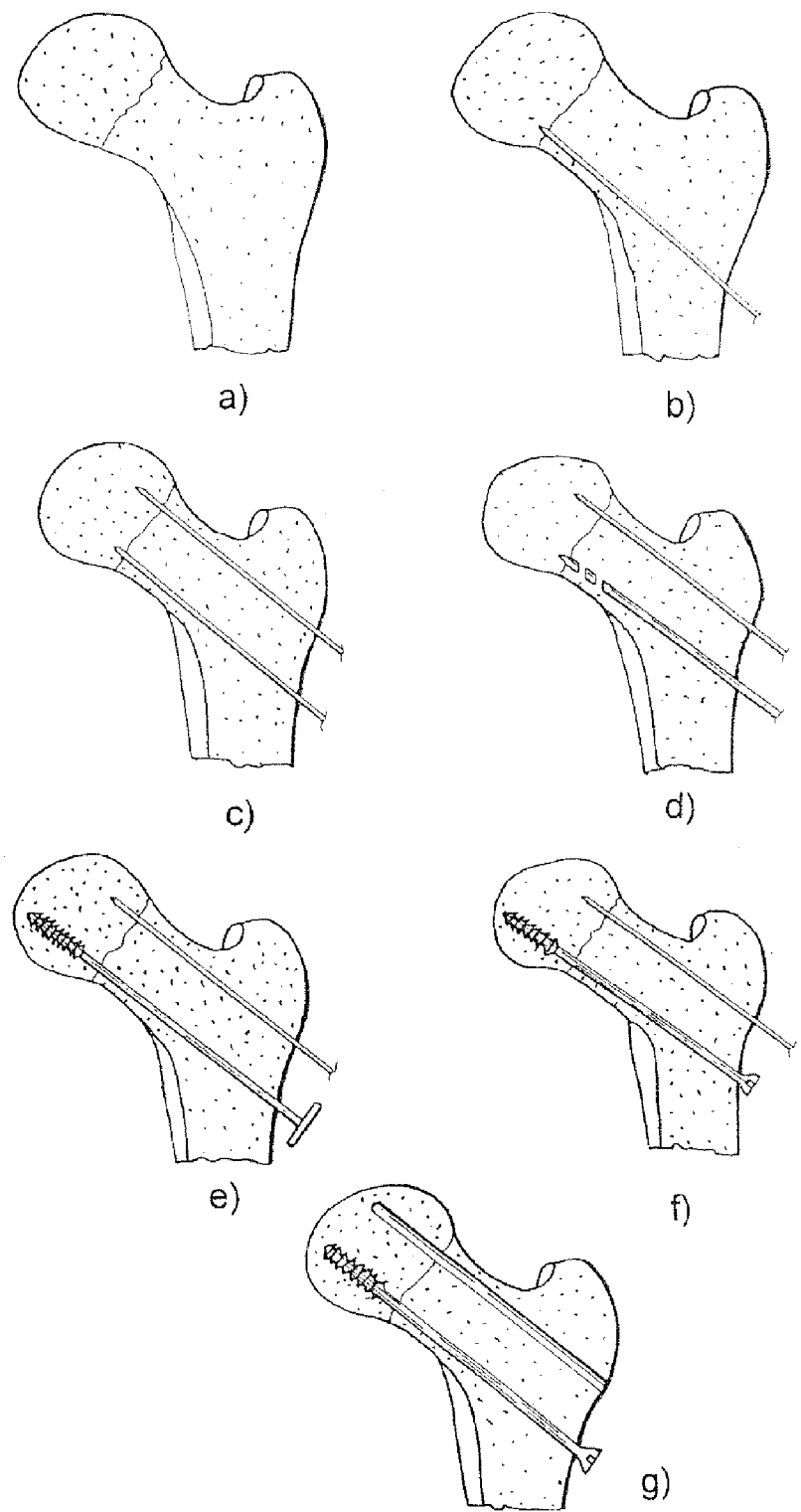
FIG. 5 depicts steps of osteoscopy and the surgical intervention of the femoral neck fracture in acute cases, as outlined in figure (a)-(m), chronologically in accordance with various embodiments of the present invention.
Figures 5A, 5B, 5C, 5D, 5E, 5F, 5G, 5H, 5I, 5J, 5K, 5L, 5M:
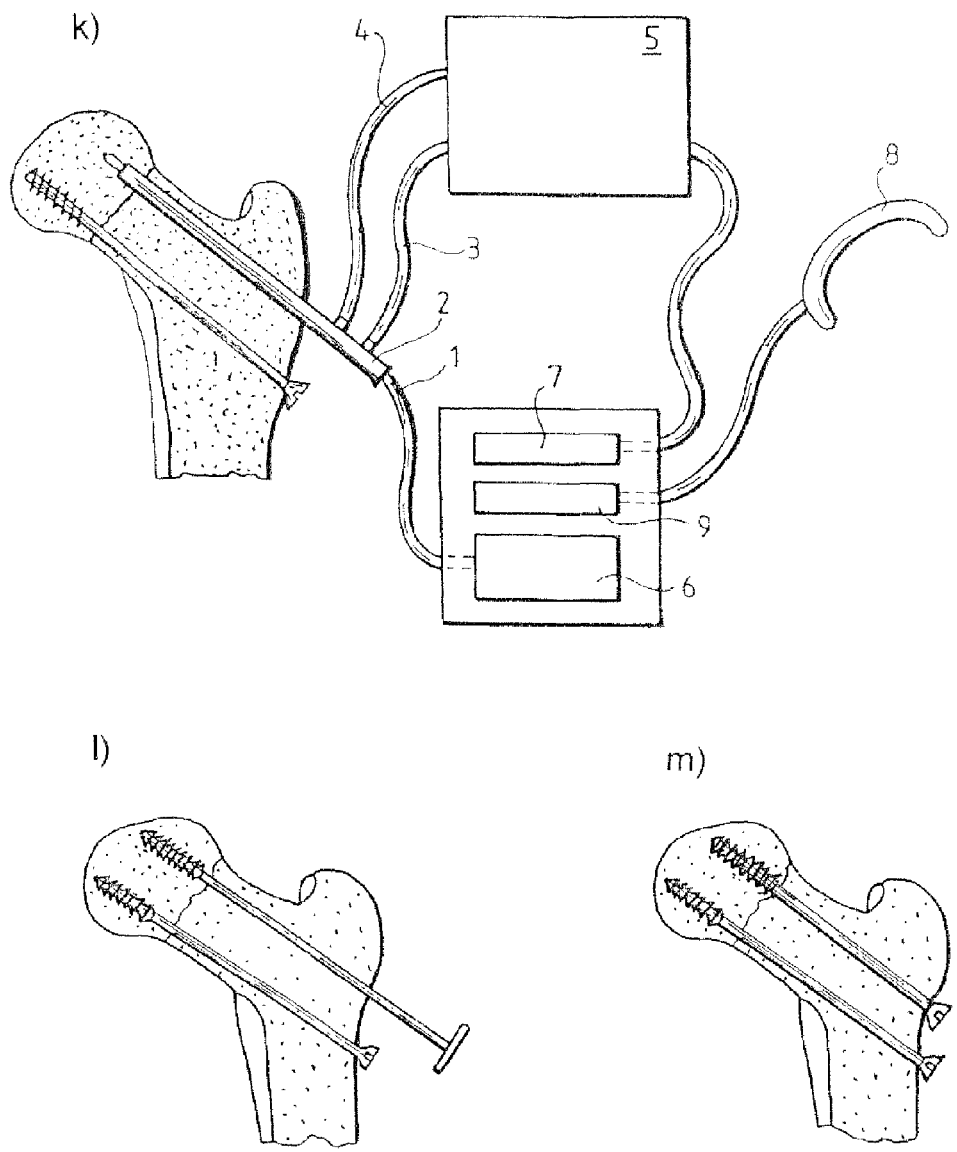

As depicted in FIG. 5 (a), the first step of the method according to the invention is to repose the fracture. In step (b), a Kirschner wire is inserted into the femoral head, and in (c) a second Kirschner wire is inserted into the femoral head. The insertion of the Kirschner wires fix the femoral head. In step (d), a hole is drilled into the femoral head. The Kirschner-wire is used as a guide for drilling. Then, a thread is cut into the hole that has been created (e), and a screw is driven into the hole for the fixation of the fracture (f). After the fracture is fixed by one screw, a second hole is drilled through the neck of the femur into the head, parallel with the neck axis, in the former place of the Kirschner wire that has been removed (g). A "thicker" drill bit, that is used for that, has an external diameter D1 approximately of the same size as the external diameter of the sleeve of the osteoscope, and the end of the drill is of a thinner diameter D2. The metal sleeve of the osteoscope is then inserted into the hole (h). A "thinner" drill is applied through the tube of the sleeve (i). The diameter D3 of the drill is approximately the same as the internal diameter of the sleeve of the osteoscope, and the end of the drill is of a thinner diameter D2. This "thinner" drill is 1.5 mm longer than the sleeve of the osteoscope. The use of the "thinner" drill allows the removal of the small bone fragments from the sheath. The end of the drill excavates a small cavity into the bone. The shape and measurements at the end of the drills are the same for both the thicker and thinner drills.

The optics of the osteoscope is inserted into the sleeve, as depicted in FIG. 5 (j and k). The small hole is in the focus of the optics. The surface of the small part of the cavity is at least 30 $mm^2$ preferably at least 35 $mm^2$, most preferably at least 40 $mm^2$.

The system is filled up with physiological solution and the blood is rinsed out of the visual scope. The pressure of the physiological solution is increased above the systolic blood pressure. While the small hole is being observed through the osteoscope, the pressure is being decreased continuously, and at the commencement of bleeding, the pressure in the system is measured.

If the circulation is acceptable, the difference between the systolic pressure and the pressure in the head is less than 60 Hg mm, and the surgical intervention is osteosynthesis (ie the femoral head preservation).

In this instance, the second screw is inserted to fix the fracture (l and m). The final result in this scenario is the fracture fixed with screws.

The method includes the use of two drills. The external diameter of one drill is approximately the same size as the external diameter of the metal sleeve; the external diameter of the second drill is approximately the same size as the inner diameter of the metal sleeve. The end sections of the drills are thinner, enabling them to create a small cavity in the bone, as shown in FIGS. 5 j and k. The length of the end sections is preferably at least 1 mm.

A commercially available endoscope with 0° optics can be used for purposes described herein. The optics of the osteoscope should be at least 400 mm long, preferably 450 mm long and most preferably 500 mm long.

The metal sleeve has two connections and a reservoir with physiological solution. The pressure of the solution is controlled by a manometer.

Returning to FIG. 5 (k), one can see, that the device includes an osteoscope, the optics 1 of which is inserted into a metal sleeve 2 well known in the art. The metal sleeve 2 has two connections: flow in connection 3 and flow out connection 4. Through these connections the device is connected to reservoir 5 with physiological solution. The device is provided with means for producing and a manometer for measuring pressure in the system. It should preferably contain a flushing fluid pump and a flushing fluid collection container as well.

The optics 1 is inserted into the sleeve 2 to be about 2 mm shorter, than the sleeve, as shown in FIG. 5 (*k*). At the other end, the optics is connected to a display 6 showing the inside of the small cavity in the bone. The display unit also contains screen 7 for the manometer showing the pressure of the physiological solution.

The device is further provided with a cuff 8 for monitoring the blood pressure of the patient. Screen 9 in the display unit shows the value of the blood pressure. It is advantageous if the device contains a computer unit for controlling the system and for recording the results.

Acceptable circulation is when the difference between the systolic pressure and the measured pressure is less than 60 mm Hg. If the difference in the pressure is more than 60 mm Hg, the surgical intervention may be the implantation of a prosthesis. If this is not the case, the surgical intervention may be femoral head preservation.

According to the present invention, the method of treatment of bone fractures, preferably femoral neck fracture is measuring circulation of blood in the femoral head and thereafter surgically performing either femoral head preservation (if there is adequate circulation) or implantation of a prosthesis (if there is inadequate circulation).

It will be readily apparent to those of skilled in the art that the inventive devices and methods can be used to measure blood pressure in any number of bones. The invention is by no means limited to the measurement of blood flow in the femur.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Steps of Osteoscopy (1) Repose the fracture. (2) Insert a Kirschner wire into the femoral head. (3) Insert a second Kirschner wire into the femoral head. The insertion of the Kirschner wires fix the femoral head. (4) Drill a hole into the femoral head. The Kirschner-wire is used as a guide for the drilling. (5) Cut a thread into the hole that has been created. (6) Drive a screw into the hole for the fixation of the fracture. (7) After the fracture is fixed by one screw, drill a second hole through the neck of the femur into the head, parallel with the neck axis, in the former place of the Kirschner wire that has been removed. Here a "thicker" drill is used, where the external diameter of the bit is of the same size as the external diameter of the sleeve of the osteoscope, and the end of the drill is a thinner diameter. (8) Insert a metal sleeve of a osteoscope into the hole. The "thinner" drill is applied through the tube of the sleeve so that in this way, bone fragments are removed. Here a "thinner" drill is used, which is 1.5 mm longer than the sleeve. The end of the drill excavates a small cavity into the bone. (9) Insert the optics of anosteoscope into the sleeve, so that the small cavity previously created is in the focus of the osteoscope. (10) Fill up the system with physiological solution and rinse blood out of the visual scope. (11) Increase the pressure of the physiological solution so that it is above the systolic blood pressure. While the small hole is being observed through the osteoscope, the pressure is being decreased continuously, and at the commencement of bleeding, the pressure in the system is measured.

Example 2

Determining Circulation Conditions from Differences in Pressure

The inventors determine excellent circulation of a femoral head if the difference between systolic pressure and the pressure in the head is lower than 30 hg mm. Average circulation of a femoral head is determined if the difference between the systolic pressure and the pressure in the head is lower than 60 hg mm but 30 hg mm or higher, Minimal circulation of a femoral head is determined if the difference between systolic pressure and the pressure in the head is 60 hg mm or higher.

Example 3

Surgical Intervention of a Femoral Neck Fracture

If the circulation is acceptable, the surgical intervention is osteosynthesis (ie the femoral head preservation). In this instance, a second screw is inserted to fix the fracture. If there is no circulation or the circulation is minimal, the screw and the femoral head are removed and prosthesis is implanted.

While the description above refers to particular embodiments of the present invention, it should be readily apparent to people of ordinary skill in the art that a number of modifications may be made without departing from the spirit thereof. Preferably, the device is provided with means (e.g. computer unit) for controlling and monitoring the method, as well as for storing and processing the data obtained during the use of the device. The presently disclosed embodiments are, therefore, to be considered in all respects as illustrative and not restrictive.

I claim:

1. A method for determining circulation of blood flow in a bone after a femoral neck fracture, comprising:
    a) drilling a hole into the bone with a drill;
    b) inserting a metal sleeve of an osteoscope into the hole;
    c) inserting optics of the osteoscope into the metal sleeve, the optics being focused on a cavity created by the drill;
    d) filling the device and the cavity with a physiological solution such that a pressure of the solution is above a systolic blood pressure of a patient;
    e) decreasing the pressure of the solution while observing the cavity through the osteoscope;
    f) recording a system pressure when bleeding commences; and
    g) determining acceptable circulation when a difference between the systolic pressure and the pressure recorded in step f) is less than 60 mm Hg, and unacceptable circulation when a difference in the pressure is more than 60 mm Hg.

2. The method as claimed in claim 1, wherein the metal sleeve is inserted into the hole to leave free the wall of a small part of the cavity.

3. The method as claimed in claim 2, wherein a diameter of the small part of the cavity is drilled to be smaller, than an internal diameter of the sleeve.

4. The method as claimed in claim 2, wherein a surface of the small part of the cavity is at least 35 mm$^2$.

5. The method as claimed in claim 2, wherein a surface of the small part of the cavity is at least 30 mm$^2$.

6. The method as claimed in claim 1, wherein the optics is arranged in the sleeve to be about 2 mm shorter, than the sleeve.

7. The method as claimed in claim 1, wherein a second drill is applied through the hole of the sleeve thereby removing fragments of the bone.

8. The method as claimed in claim 1, wherein the hole is flushed out with physiological solution, after step b).

9. The method as claimed in claim 8, wherein the drill is provided with an external diameter approximately the same size as an external diameter of the sleeve.

10. The method as claimed in claim 9, wherein the drill is provided with an end section having smaller diameter, than the internal diameter of the sleeve.

11. A device for determining blood flow in a bone after a femoral neck fracture, comprising:
   a metal sleeve of an osteoscope to be inserted into a bore drilled in the fractured bone;
   an optics of an osteoscope to be inserted into said metal sleeve and connected to a visual display of the osteoscope;
   a reservoir with physiological solution connected to the metal sleeve;
   means for controlling the pressure of the solution;
   a manometer for monitoring the pressure of the solution; and
   a manometer for measuring the blood pressure of the patient,
   wherein the device is configured for determining acceptable circulation when a difference between a systolic pressure of a patient and a system pressure recorded when bleeding commences is less than 60 mm Hg, and unacceptable circulation when a difference in the pressure is more than 60 mm Hg.

12. The device as claimed in claim 11, wherein the metal sleeve has a flow in connection and a flow out connection to the reservoir with physiological solution.

13. The device as claimed in claim 11, wherein a drill is provided with an external diameter approximately the same size as an internal diameter of the sleeve.

14. The device as claimed in claim 13, wherein the end section is at least 1 mm long.

15. The device as claimed in claim 11, wherein the osteoscope is an osteoscope with 0° optics.

16. The device as claimed in claim 11, wherein the osteoscope is at least 150 mm long.

17. The device as claimed in claim 11, wherein the device contains a flushing fluid pump and a flushing fluid collection container.

* * * * *